United States Patent [19]

Kump et al.

[11] Patent Number: 4,876,258
[45] Date of Patent: Oct. 24, 1989

[54] BIPHENYLYL COMPOUNDS

[75] Inventors: Wilhelm Kump, Biel-Benken; Peter Traxler, Schönenbuch, both of

[73] Assignee: Ciba-Geigy Corporation, Ardsley, N.Y.

[21] Appl. No.: 226,487

[22] Filed: Aug. 1, 1988

[30] Foreign Application Priority Data

Aug. 13, 1987 [CH] Switzerland ............... 3124/87

[51] Int. Cl.$^4$ ................. A61K 31/495; C07D 405/14
[52] U.S. Cl. ...................................... 514/254; 540/458
[58] Field of Search .................... 540/458; 514/254

[56] References Cited

U.S. PATENT DOCUMENTS

| | | | |
|---|---|---|---|
| 3,342,810 | 9/1967 | Maggi et al. | 260/239.3 |
| 3,524,845 | 8/1970 | Bickel et al. | 540/458 |
| 3,644,337 | 2/1972 | Bickel et al. | 540/458 |
| 4,005,077 | 1/1977 | Bickel et al. | 260/239.3 P |
| 4,193,920 | 3/1980 | Konstantinova et al. | 540/458 |
| 4,353,826 | 10/1982 | Bickel et al. | 514/924 |
| 4,551,450 | 11/1985 | Traxler | 514/183 |
| 4,681,938 | 7/1987 | Traxler | 540/458 |
| 4,774,237 | 9/1988 | Ueno et al. | 540/458 |

FOREIGN PATENT DOCUMENTS

WO87/02361 4/1987 PCT Int'l Appl. .

*Primary Examiner*—Robert T. Bond
*Assistant Examiner*—James H. Turnipseed
*Attorney, Agent, or Firm*—Irving M. Fishman; JoAnn Villamizar

[57] ABSTRACT

Rifamycin derivatives of formula

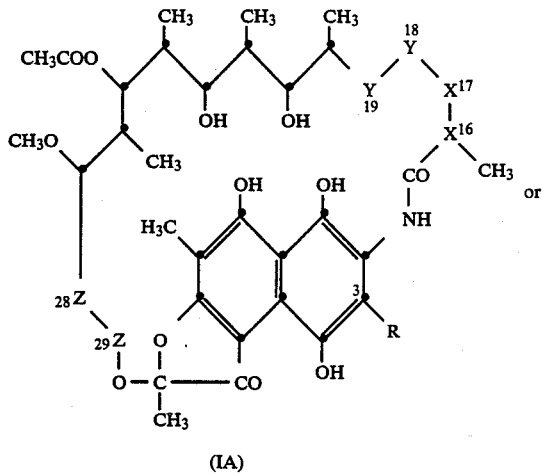

(IA)

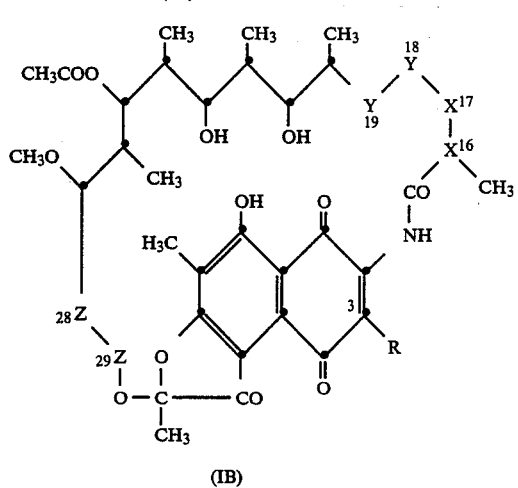

(IB)

wherein R is a radical of the formula

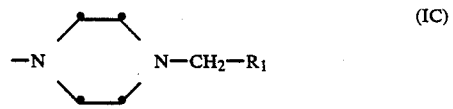

(IC)

in which $R_1$ is an unsubstituted or substituted biphenylyl radical, and wherein X—X, Y—Y and Z—Z are each vinylene of the formula CH=CH, or wherein X—X and Y—Y are each ethylene of the formula $CH_2$—$CH_2$ and Z—Z is ethylene or vinylene, and processes for the preparation thereof are described. These compounds can be used as antibacterial and antiviral medicaments.

12 Claims, No Drawings

BIPHENYLYL COMPOUNDS

The present invention relates to novel derivatives of rifamycin SV and S having antibiotic activity. The derivatives in question are rifamycin compounds that contain a 4-substituted 1-piperazinyl radical in the 3-position and have the formula

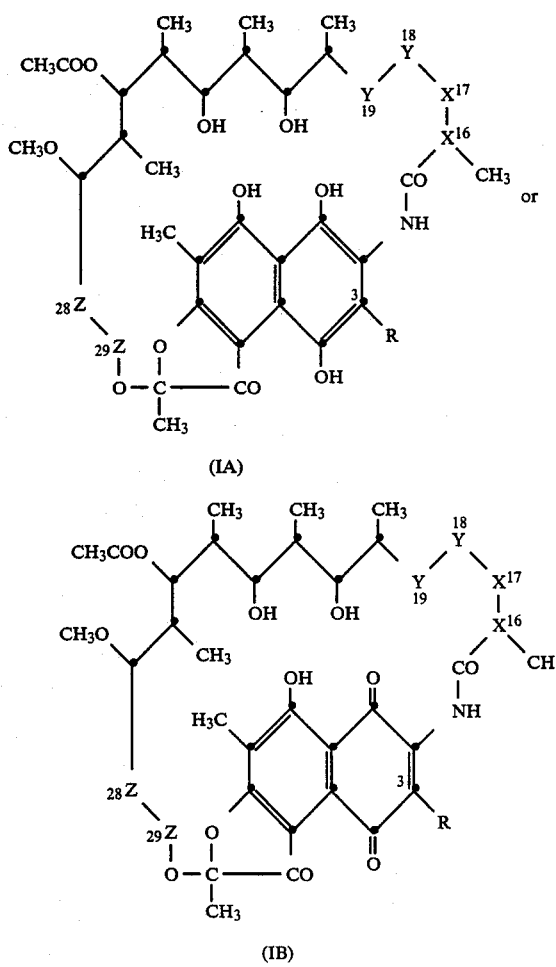

wherein R is a radical of formula

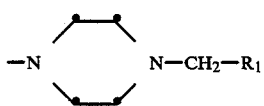

(IC)

in which $R_1$ is an unsubstituted or substituted biphenylyl radical, and wherein X—X, Y—Y and Z—Z are each vinylene of the formula CH=CH, or wherein X—X and Y—Y are each ethylene of the formula $CH_2$—$CH_2$ and Z—Z is ethylene or vinylene, and salts of such compounds.

The invention further relates to processes for the preparation of the compounds of formulae IA and IB and their salts, to pharmaceutical preparations containing them and to the us of these compounds and preparations.

The numbering employed in this specification refers to that used, for example, in U.S. Pat. No. 4,005,077.

Because of the close relationship between the 1,4-quinone and 1,4-hydroquinone forms (corresponding to rifamycin S and SV) and the ease with which the two forms change into each other, unless specified otherwise both forms are part of the invention, but the SV form (IA) is to be regarded as the preferred form.

The unsubstituted or substituted biphenylyl radical $R_1$ may be a corresponding 3-biphenylyl, preferably a corresponding 2-biphenylyl and especially a corresponding 4-biphenylyl radical, which biphenylyl radicals may be substituted, for example, by lower alkyl, preferably containing from 1 to 4 carbon atoms, such as methyl, ethyl, n-propyl, isopropyl, n-butyl, isobutyl or tert.-butyl, lower alkoxy, preferably containing from 1 to 4 carbon atoms, for example methoxy, ethoxy or isopropoxy, or by halogen, preferably, for example, fluorine or chlorine, or also bromine, it being possible for one or more identical or different substituents to be present in one aromatic ring or in both aromatic rings of the biphenylyl group $R_1$.

Unless defined otherwise, radicals referred to as "lower" are to be understood, for example, as those containing up to and including 7, especially up to and including 4, carbon atoms.

Salts of compounds of formulae IA and IB are especially acid addition salts, especially therapeutically acceptable acid addition salts; hydroquinone compounds of formula IA can also form salts with bases.

These compounds of formulae IA and IB exhibit, inter alia, antibacterial activity, especially towards mycobacteria, as can be demonstrated, inter alia, in mice or rats infected, for example, with Mycobacterium tuberculosis In such tests, they exhibit $ED_{50}$ values that approximately correspond to those of the known antituberculous agent rifampicin.

Although rifampicin is one of the preferred agents for the treatment of tuberculous infections especially, its relatively short retention time in the organism is a significant disadvantage in some cases. The provision of active substances having an activity against tuberculosis infections that is approximately equal to, but at the same time more prolonged than, that of rifampicin is therefore a matter of pressing importance. The 3-(4-benzyl-1-piperazinyl)-rifamycins described, for example, in U.S. Pat. No. 4,005,077 do not have the desired advantage; although their antituberculous activity in vivo is approximately 3 times that of rifampicin, they are barely superior to rifampicin with regard to prolonged activity.

In contrast, it has now been found that the novel compounds according to the present invention are surprisingly distinguished not only by good antituberculous activity, which approximately corresponds to that of rifampicin, but also, especially, by a considerably increased retention time in the organism.

In addition, the compounds of the present invention exhibit a surprisingly high activity, compared with that of rifampicin, towards atypical mycobacteria, especially towards M. avium, such as M. avium complex, for example in doses of approximately 0.01 μg/ml and above. Infections that are attributable to atypical mycobacteria, especially M. avium, have been detected especially in patients suffering from the so-called "Acquired Immune Deficiency Syndrome" (AIDS) and are often the direct cause of death in such patients.

The novel compounds of the present invention, especially those in which X—X and Y—Y are ethylene and Z—Z is ethylene or vinylene, whose activity towards mycobacteria, including atypical mycobacteria, is not so pronounced, also inhibit, in doses of approximately 0.5 μg/ml and above, reverse transcriptase, which is an enzyme that is characteristic of retroviruses (or oncornaviruses), such as RNA tumour viruses and leukaemia viruses. Retroviruses need this enzyme for their natural replication cycle.

In humans, type C retroviruses and their reverse transcriptase were first detected in a T-cell leukaemia; the virus was named human T-cell leukaemia virus (HTLV-I). The same virus and a similar retrovirus (HTLV-II) were found in other T-cell leukaemias and lymphomas. Lastly, such a virus was also isolated in connection with AIDS. That virus was initially called HTLV-III or LAV; the name currently used for this group of viruses is HIV. These retroviruses belonging to the HTLV family need reverse transcriptase for the formation of a double-strand DNA (provirus) that is "integrated" into the cell genome and may result in malignant transformation.

Whereas, after the induction of malignant leukaemic, lymphatic or tumorous neoplasms by retroviruses, a reduction in reverse transcriptase and HTLV-I and HTLV-II virus can be detected, and secondary oncogenes induced by these viruses control the replication of the malignant cells, in the case of AIDS the HIV virus and reverse transcriptase can be detected not just in the early stages but throughout the entire course of the disease. The continuous infection and the functional disturbance of immuno-competent T-helper cells finally result in the breakdown of the immune system. It is to be assumed that, when enzyme- and virus-antigen detection is positive, inhibition of reverse transcriptase and therewith of virus replication will influence the course of the disease. On the other hand, in the case of induction of leukaemias and lymphomas by retroviruses (HTLV-I and HTLV-II), and possibly also in the case of sarcomas and mammary carcinomas induced by retroviruses, prophylactic use should be possible provided that there is a readily and widely available method of diagnosing those patients at risk.

Reverse transcriptase has also been found as a specific enzyme in association with virus particles in connection with non-A-hepatitis and non-B-hepatitis.

In addition, the novel compounds of the present invention exhibit good antibacterial properties towards other microorganisms, especially gram-positive microorganisms. For example, in in vitro testing they exhibit inhibitory activity towards estaphylococci, such as Staphylococcus aureus K 1098, and towards streptococci, such as Streptococcus pyogenes Aronson K 1129, at approximately 0.005 μg/ml and above. In in vivo tests, for example against the above-mentioned Staphylococcus, the compounds of the present invention are active in doses (ED$_{50}$) of approximately 1 mg/kg and above both when administered subcutaneously and when administered orally.

At the same time, the compounds according to the present invention have a broad therapeutic range since only at very high doses, for example of the order of 5000 mg/kg, do they exhibit significant toxicity.

The novel compounds can therefore be used as medicaments, especially for the treatment of bacterial, usually tuberculous, diseases, especially those caused by atypical mycobacteria, and viral diseases, especially those caused by type C retroviruses, such as viruses of the HTLV and HIV type, especially in the treatment of AIDS sufferers, it being possible to use the novel compounds prophylactically or therapeutically. The principal use of the compounds of the present invention in this context is in the treatment of malignant diseases that are caused by atypical mycobacteria, especially M. avium, and by type C retroviruses, or in which such mycobacteria and retroviruses are a contributory cause, and in the treatment of certain immune diseases and autoimmune diseases. Tumour diseases to be mentioned are especially leukaemias, lymphomas and lymphosarcomas caused by retroviruses, and, possibly, also osteosarcomas and mammary carcinomas, the compounds of the present invention being suitable also for preventing relapse following surgery, radiation therapy or cytostatic or antimetabolic chemotherapy. AIDS may be mentioned as an immune disease, and systemic lupus erythematosus as an autoimmune disease, in which, according to recent findings, RNA tumour viruses also appear to play an important role.

The compounds according to the invention can also be used as starting materials for the preparation of valuable pharmaceuticals.

The invention relates especially to compounds of formulae IA and IB wherein R is a radical of formula IC in which $R_1$ is biphenylyl which is unsubstituted or is substituted by lower alkyl, lower alkoxy and/or by halogen, wherein lower alkyl and lower alkoxy preferably contain up to and including 4 carbon atoms and are especially methyl and methoxy, respectively, and halogen is especially fluorine or chlorine, and wherein biphenylyl is preferably 2-biphenylyl and especially 4-biphenylyl, and wherein X—X, Y—Y and Z–Z are as defined above, and to salts, especially pharmaceutically acceptable salts, of such compounds.

The invention relates preferably to compounds of formulae IA and IB wherein R is a radical of formula IC in which $R_1$ is biphenylyl, especially 2-biphenylyl and more especially 4-biphenylyl, which is unsubstituted or is substituted by lower alkyl containing up to and including 4 carbon atoms, especially methyl, and/or by halogen, especially fluorine or chlorine, and wherein X—X, Y—Y and Z—Z are vinylene, or X—X and Y—Y are ethylene and Z—Z is vinylene or ethylene, and to salts, especially pharmaceutically acceptable salts, of such compounds.

The invention relates more especially to compounds of formula IB, and preferably of formula IA, wherein R is a radical of formula IC in which $R_1$ is 4-biphenylyl substituted by methyl or is especially unsubstituted 4-biphenylyl, and wherein X—X, Y—Y and Z—Z are vinylene or X—X and Y—Y are ethylene and Z—Z is vinylene or ethylene, and to salts, especially pharmaceutically acceptable salts, of such compounds.

The invention relates most especially to 3-[4-(4-biphenylyl-methyl)-1-piperazinyl]-rifamycin SV and to the corresponding 3-[4-(4-biphenylyl-methyl)-1-piperazinyl]-16,17,18,19-tetrahydro-rifamycin SV and -16,17,18,19,28,29-hexahydro-rifamycin SV, and to salts, especially pharmaceutically acceptable salts, of such compounds.

The novel compounds according to the invention of formulae IA and IB can be prepared analogously to processes that are generally known per se, for example (a) by reacting a 3-$R_o^1$-rifamycin S or 3-$R_o^1$-rifamycin SV or a corresponding 16,17,18,19-tetrahydro or 16,17,18,-19,28,29-hexahydro compound, wherein $R_o^1$ is N-piper-azinyl, with an agent that introduces a radical of the formula —CH$_2$—R$_1$ (IIIA), or (b) for the preparation of a compound of formula (IB), by reacting a 3-$R_o^2$-rifamycin S or a 16,17,18,19-tetrahydro or 16,17,18,19,28,29-hexahydro derivative thereof, wherein $R_o^2$ is hydrogen or halogen, with a compound of formula

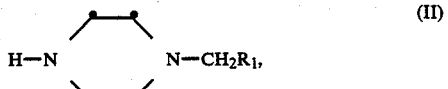

(II)

and, if desired, converting a compound of formula (IA) and/or (IB) obtainable in accordance with the process into a different compound of formula (IA) and/or (IB), and/or converting a salt obtainable in accordance with the process into the free compound or into a different salt and/or converting a free compound obtainable in accordance with the process into a salt.

Reagents used in Process variant (a) for introducing the radical of formula IIIA are reactive esters of the corresponding alcohol, especially compounds of formula $X-CH_2-R_1$ (III), wherein X is the radical of a strong inorganic or organic acid, such as the radical of a hydrohalic acid, such as hydrochloric, hydrobromic or hydriodic acid, or of an oxygen-containing inorganic acid, such as sulfuric acid, phosphoric acid, phosphorous acid, silicic acid or sulfurous acid, or of a halosulfuric acid, such as fluorosulfonic acid, or of an organic sulfonic acid, such as an aliphatic or aromatic sulfonic acid, for example a lower alkanesulfonic acid, such as methanesulfonic acid, or of an unsubstituted or, for example, lower alkyl- or nitro-substituted benzenesulfonic acid, such as p-toluenesulfonic acid or 4-nitrobenzenesulfonic acid. X is especially chlorine, bromine or iodine, or also methanesulfonyloxy or p-toluenesulfonyloxy The reaction is preferably effected in the presence of a base, especially a strongly basic, non-nucleophilic, tertiary amine, preferably a corresponding sterically hindered aliphatic and/or araliphatic amine, such as a tri-lower alkylamine, for example the so-called Hünig base, i.e. ethyldiisopropylamine. The rifamycin starting material and the alkylating agent ar used in approximately equimolar amounts, it being preferable for the base to be added also in an equimolar ratio.

The reaction is preferably carried out in the presence of a suitable solvent or mixture of solvents and, if necessary, with cooling or heating, for example in a temperature range of from approximately 0° C. to approximately +100° C., and/or in an inert gas atmosphere.

Process variant (b) is carried out in a manner known per se. For example, in the reaction with starting materials of the 3-$R_o^2$-rifamycin S type, wherein $R_o^2$ is hydrogen or halogen, an excess, for example approximately a 5- to 10-fold excess, of a compound of formula II is advantageously used. The reaction is carried out, for example, in an organic solvent that is free of hydroxy groups and is preferably of low polarity, such as a halogenated aliphatic hydrocarbon, such as methylene chloride or chloroform, an ester or ether, such as, for example, ethyl acetate, butyl acetate, amyl acetate, 1,2-dimethoxyethane or tetrahydrofuran, and especially in dioxan, or in a solvent mixture and preferably at room temperature or, for example, if the reaction is proceeding too slowly, at elevated temperature, for example up to 100°, if necessary in an inert gas atmosphere. The course of the reaction can be monitored by thin-layer chromatography.

In this process variant, a mixture of the desired reaction product in the quinone (formula IB) and the hydroquinone (IA) form is generally formed. This mixture is preferably rendered homogeneous, as described in detail hereinbelow, it being possible to form the hydroquinone form (derivative of the SV series) by means of reduction and the quinone form (derivative of the S series) by means of oxidation.

In 3-$R_o^2$-rifamycin S starting materials in which $R_o^2$ is halogen, apart from being, for example, chlorine or iodine, $R_o^2$ is especially bromine. The reaction with a compound of formula II is usually carried out in an inert solvent, especially an ether, such as tetrahydrofuran or dioxan, or in a halogenated aliphatic hydrocarbon, such as chloroform, dichloromethane or 1,2-dichloroethane, or in an aromatic hydrocarbon, such as benzene or toluene, or in a mixture thereof, the reaction being performed, if necessary, with cooling or heating, preferably at temperatures in the range of from 0° C. to 100° C., and, if necessary, in an inert gas atmosphere.

The conversion of compounds of formulae IA and IB into different compounds of formulae IA and/or IB can be effected in a manner known per se.

For example, compounds of formulae IA and IB wherein X—X and Y—Y are ethylene and Z—Z is ethylene or vinylene can be obtained by saturating the double bonds of the vinylene groups in a compound of formula IA or IB wherein X—X, Y—Y and Z—Z are vinylene or X—X and Y—Y are ethylene and Z—Z is vinylene.

Saturation of the double bonds is carried out in a manner known per se, usually by means of catalytic hydrogenation. For this, hydrogen is used under normal or elevated pressure under heterogeneous or homogeneous catalysis conditions. Suitable catalysts for the former are metal catalysts, for example Raney metals, such as Raney nickel, or noble metal catalysts, such as palladium, platinum, platinum oxide or rhodium which may be adsorbed on a carrier, such as calcium carbonate or barium sulphate. For homogeneous catalysis there are used, especially, complex rhodium compounds, for example tris(triphenylphosphine)rhodium(I) chloride.

The hydrogenation conditions can be modified in such a manner that the less reactive, isolated 28,29-double bond is not simultaneously reduced, for example by discontinuing the hydrogenation when two equivalents of hydrogen have been consumed and isolating the resulting 16,17,18,19-tetrahydro derivative. For this purpose, a milder catalyst is used, such as, for example, palladium on a carrier, for example activated carbon or calcium carbonate, in which case, under normal pressure and room temperature, the reaction comes to a standstill spontaneously when two equivalents of hydrogen have been consumed. When stronger catalysts are used, for example platinum, especially in the form obtainable in situ from platinum oxide by reduction, the hydrogenation may result in saturation of all three double bonds; under the conditions customarily used, the hydrogenation comes to a standstill spontaneously and the corresponding 16,17,18,19,28,29-hexahydro derivative is formed.

Hydrogenation gives rise to a centre of asymmetry at carbon atom 16 and thus to a mixture of epimers that differ from each other by the steric arrangement of the methyl group bonded to carbon atom 16. Since separation of the epimers by physical methods is difficult and, in addition, involves high losses, the epimeric mixture obtained is usually isolated and used as a homogeneous process product.

The process products can be obtained either in the hydroquinone form of formula IA or in the quinone form of formula IB or, especially in the case of the product of process modification b), in the form of a mixture of the two forms; they can subsequently be converted into each other, or a mixture of the two forms can subsequently be converted into one of the two homogeneous forms in a manner known per se. The conversion may be carried out by means of reduction or oxidation, as appropriate, after or, advantageously, before isolation of the desired product. The reduction of a quinone to the corresponding hydroquinone can be carried out by treatment with a suitable reducing agent, such as an alkali metal dithionite or hydrosulfite, for example sodium dithionite or hydrosulfite, with zinc and acetic acid, or preferably with ascorbic acid, and the oxidation of a hydroquinone to the corresponding quinone can be carried out by treatment with a suitable oxidising agent, such as atmospheric oxygen, hydrogen peroxide, an alkali metal ferricyanide, for example potassium ferricyanide, a persulfate, for example ammonium persulfate, or manganese dioxide, the oxidation preferably being carried out under basic conditions. The quinones are for the most part violet-red to black compounds, whereas the hydroquinones are usually pale, for example yellow, in color and usually crystallise better.

The isolation of the reaction products from a reaction mixture obtainable in accordance with the process is carried out in a manner known per se, for example by diluting with water, and/or, where appropriate, by neutralising with an aqueous acid, such as an inorganic or organic acid, for example a mineral acid or citric acid, and by adding a water-immiscible solvent, such as, for example, a chlorinated hydrocarbon, for example chloroform or methylene chloride, the reaction product passing into the organic phase from which it can be obtained in pure form in customary manner, for example after drying by concentrating the solvent by evaporation and crystallisation and/or chromatography of the residue or other customary purification methods.

The compounds of the present invention can form salts, especially acid addition salts and more especially pharmaceutically acceptable acid addition salts, with inorganic or organic acids. Such acids are, inter alia, hydrohalic acids, for example hydrochloric or hydrobromic acid, sulfuric acid, phosphoric acid, nitric acid or perchloric acid, or aliphatic, alicyclic, aromatic or heterocyclic carboxylic or sulfonic acids, such as formic, acetic, propionic, succinic, glycolic, lactic, malic, tartaric, citric, fumaric, maleic, hydroxymaleic, oxalic, pyruvic, phenylacetic, benzoic, p-aminobenzoic, anthranilic, p-hydroxybenzoic, salicylic, p-aminosalicylic, embonic, methanesulfonic, ethanesulfonic, hydroxyethanesulfonic, ethylenedisulfonic, halobenzenesulfonic, toluenesulfonic, naphthalenesulfonic or sulfanilic acid, and methionine, tryptophan, lysine or arginine, and also ascorbic acid. Hydroquinone compounds of the formula IA type can also form salts with bases, for example alkali metal salts, such as sodium or potassium salts.

Salt formation, and the freeing of the compounds of formulae IA and IB from their salts, is carried out in a manner known per se. For example, hydroquinones of formula IA can be converted into corresponding salts with bases, especially alkali metal salts, by treatment with a corresponding base, especially a suitable alkali metal hydroxide, carbonate or hydrogen carbonate; the corresponding salts can be converted into the free hydroquinone compounds by acidification, for example with inorganic acids, such as, for example, a hydrohalic acid. Basic end products can be converted into their acid addition salts, for example by treatment with an acid suitable for forming salts, such as one of the acids mentioned above; it is possible to obtain the free compounds from the acid addition salts by treatment with basic agents, such as inorganic hydroxides, carbonates and hydrogen carbonates, or organic bases or ionexchangers.

Compounds of the present invention can also form internal salts, which can be obtained, for example, by customary titration to the neutral point or to the isoelectric point.

These or other salts, such as, for example, the picrates, can also be used for purifying the resulting compounds by converting the free compounds into salts, separating the latter and recovering the free compounds from the salts. In view of the close relationship between the compounds in free form and in the form of their salts, throughout this specification the free compounds shall also be understood as meaning, where appropriate, the corresponding salts.

The invention relates also to those embodiments of the process according to which a compound obtainable as a intermediate at any stage of the process is used as starting material and the remaining steps are carried out, or a starting material is used in form of a derivative, for example a salt, or is formed under the reaction conditions.

The starting materials used in the processes of the present invention are preferably those which result in the compounds described at the beginning as being especially valuable.

The starting materials used in the process described above are known or can be prepared in a manner known per se.

For example, the starting materials for process variant (a) can be obtained by treating rifamycin S with piperazine in which one of the ring nitrogen atoms may be protected by a readily removable protecting group, such as an acyl radical that can be removed by hydrolysis, for example lower alkoxycarbonyl, such as methoxycarbonyl or ethoxycarbonyl, or a benzyl radical that can be removed by hydrogenolysis, and, if necessary, subsequently removing any protecting group present in the piperazine radical by means of, for example basic, hydrolysis or hydrogenolysis, for example with hydrogen in the presence of a hydrogenation catalyst; this operation can be carried out, for example, in accordance with the process described above for variant (b). A resulting 3-$R_o^1$-rifamycin S compound can be converted into the corresponding 3-$R_o^1$-rifamycin SV compound in accordance with the process described above by means of reduction, for example by treatment with ascorbic acid, a resulting 3-$R_o^1$-rifamycin SV compound can be converted into the corresponding 3-$R_o^1$-rifamycin S compound by means of oxidation, for example by treatment with manganese dioxide, and a resulting mixture of the two forms can be converted appropriately into the one or the other form. Starting from the corresponding 16,17,18,19-tetrahydro- or 16,17,18,19,28,29-hexahydro-rifamycin S, which can be obtained, for example, by hydrogenation, for example in accordance with the process described above, and conversion of a rifamycin SV compound into the corresponding rifamycin S compound, it is possible to obtain the corresponding 16,17,18,19-tetrahydro or 16,17,18,19,-28,29-hexahydro starting materials.

Some of the starting materials for process variant (b) are known; the 16,17,18,19-tetrahydro and 16,17,18,19-28,29-hexahydro compounds can be obtained by means of reduction, for example catalytic hydrogenation in accordance with the process described above, it being possible for rifamycin SV compounds obtainable in accordance with the process to be converted as described above into the corresponding rifamycin S compounds and vice versa.

The present invention also includes the use of the compounds according to the invention of formulae IA and IB and their pharmaceutically acceptable salts, where appropriate together with adjuncts and/or in combination with other active ingredients, especially antibiotics or chemotherapeutic agents, for the preparation of appropriate medicaments or as agents for the treatment of diseases, such as those described above, it being possible to use them both prophylatically and curatively. The active ingredients according to the invention are administered in effective amounts, preferably in the form of pharmaceutical compositions together with conventional pharmaceutical carriers or adjuncts. Depending on the species, age and individual condition and also on the mode of administration and especially also on the particular effect on the pathogen in question, the daily doses used, for example for warm-blooded animals of approximately 70 kg body weight, are from approximately 50 to approximately 3000 mg, for example 600 mg, which may be exceeded in acute cases. Accordingly, the invention includes also the corresponding method of medical treatment.

The invention further relates to pharmaceutical compositions containing the compounds of the present invention as active ingredients, and to processes for the preparation of these compositions.

The pharmaceutical compositions according to the invention are, for example, for enteral, such as peroral or rectal, administration and also for parenteral administration. Corresponding dosage unit forms, especially for peroral administration, for example dragées, tablets or capsules, preferably contain from approximately 50 to approximately 500 mg, especially from approximately 100 to approximately 300 mg, of the active ingredient, usually together with pharmaceutically acceptable carriers or adjuncts.

Suitable carriers are especially fillers, such as sugars, for example lactose, saccharose, mannitol or sorbitol, cellulose preparations and/or calcium phosphates, for example tricalcium phosphate or calcium hydrogen phosphate, and also binders, such as starch pastes (using, for example, corn, wheat, rice or potato starch), gelatin, tragacanth, methylcellulose and/or, if desired, disintegrating agents, such as the above-mentioned starches, and also carboxymethyl starch, crosslinked polyvinylpyrrolidone, agar, alginic acid or a salt thereof, such as sodium alginate Adjuncts are especially flow-regulating agents and lubricants, for example silica, talc, stearic acid or salts thereof, such as magnesium or calcium stearate, and/or polyethylene glycol. Dragée cores may be provided with suitable coatings which may be resistant to gastric juices, there being used, inter alia, concentrated sugar solutions which may contain gum arabic, talc, polyvinylpyrrolidone, polyethylene glycols and/or titanium dioxide, or lacquer solutions in suitable organic solvents or mixtures of solvents, or, for the preparation of coatings that are resistant to gastric juices, solutions of suitable cellulose preparations, such as acetylcellulose phthalate or hydroxypropylmethylcellulose phthalate. Dyes or pigments may be added to the tablets or dragée coatings, for example for identification purposes or to indicate different doses of active ingredient.

Other orally administrable pharmaceutical preparations are dry-filled capsules consisting of gelatin, and also soft sealed capsules consisting of gelatin and a plasticiser, such as glycerin or sorbitol The dry-filled capsules may contain the active ingredient in the form of a granulate, for example in admixture with fillers, such as lactose, binders, such as starches, and/or glidants, such as talc or magnesium stearate, and optionally stabilisers. In soft capsules, the active ingredient is preferably dissolved or suspended in suitable liquids, such as fatty oils, paraffin oil or liquid polyethylene glycols, to which stabilisers may also be added.

Suitable rectally administrable pharmaceutical preparations are, for example, suppositories that consist of a combination of the active ingredient with a suppository base. Suitable suppository bases are, for example, natural or synthetic triglycerides, paraffin hydrocarbons, polyethylene glycols or higher alkanols. It is also possible to use gelatin rectal capsules that contain a combination of the active ingredient with a base material; suitable base materials are, for example, liquid triglycerides, polyethylene glycols or paraffin hydrocarbons.

There are suitable for parenteral administration especially aqueous solutions of a water-soluble form of the active ingredient, for example a water-soluble salt, or aqueous injection suspensions that contain viscosity-increasing substances, for example sodium carboxymethylcellulose, sorbitol and/or dextran and, optionally, stabilisers. It is also possible for the active ingredient, where appropriate together with adjuncts, to be in the form of a lyophilisate and to be dissolved before parenteral administration by the addition of suitable solvents.

The pharmaceutical compositions of the present invention can be prepared in a manner known per se, for example by means of conventional mixing, granulating, confectioning, dissolving or lyophilising processes. For example, pharmaceutical preparations for oral administration can be obtained by combining the active ingredient with solid carriers, optionally granulating a resulting mixture and processing the mixture or granulate, if desired or necessary after the addition of suitable adjuncts, to form tablets or dragée cores.

The following Examples illustrate the invention described above, but do not limit the scope thereof in any way. Temperatures are given in degrees Celsius.

EXAMPLE 1

17.5 g of 1-(4-biphenyly-methyl)-piperazine are added to a solution of 3 g of 3-bromorifamycin S in 50 ml of tetrahydrofuran and the mixture is left to stand for 30 minutes at 20°. It is then acidified by adding aqueous citric acid solution, and the reaction product is taken up in methylene chloride. After drying and concentration of the organic extract by evaporation, a dark-coloured residue remains which is 3-[4-(4-biphenylyl-methyl)-1-piperazinyl]-rifamycin S of empirical formula $C_{54}H_{63}N_3O_{12}$. This residue is dissolved in methanol, and aqueous ascorbic acid is added dropwise thereto. 3-[4-(4-Biphenylyl-methyl)-1piperazinyl]-rifamycin SV precipitates in crystalline form, m.p. 172°–174°; mass spectrum (MS:(M+1)+)=m/e 948, corresponding to the empirical formula $C_{54}H_{65}N_3O_{12}$.

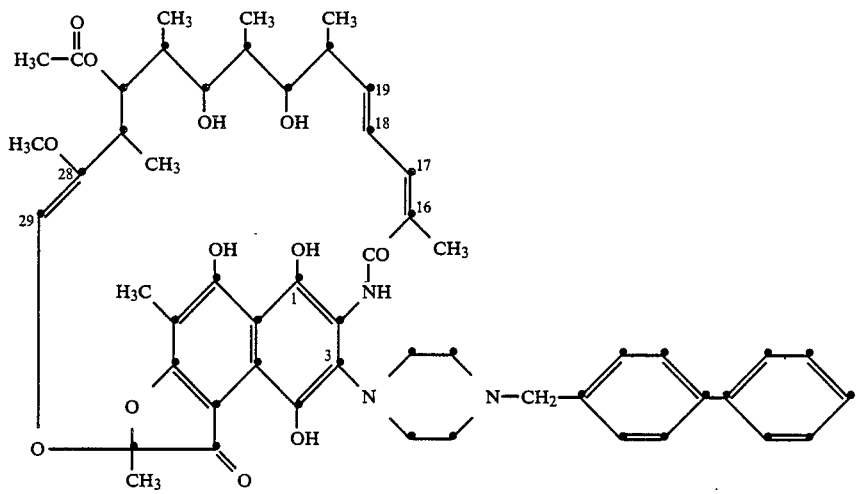

EXAMPLE 2

A mixture of 2 g of rifamycin S and 2 g of 1-(4-biphenylyl-methyl)-piperazine in 50 ml of dioxan is left to stand at room temperature for 24 hours and is then worked up analogously to the process in Example 1, including the treatment with aqueous ascorbic acid. 3-[4-(4-Biphenylyl-methyl)-1-piperazinyl]-rifamycin SV is obtained in crystalline form, m.p. 172°–174°.

In order to prepare the sodium salt, equivalent amounts of 3-[4-(4-biphenylyl-methyl)-1-piperazinyl]-rifamycin SV and sodium hydrogen carbonate are dissolved in a mixture of dioxan and water, and the solution is lyophilised.

EXAMPLE 3

A solution of 2 g of 3-[4-(4-biphenylylmethyl)-1-piperazinyl]-rifamycin SV in 100 ml of ethanol is hydrogenated in the presence of 0.2 g of 10 % (w/w) palladium-on-carbon for 5 hours at room temperature under normal pressure. The catalyst is filtered off through a layer of kieselguhr, the filtrate is concentrated to dryness by evaporation and the residue is crystallised from a mixture of ethyl acetate and diethyl ether, yielding 3-[4-(4-biphenylyl-methyl)-1-piperazinyl]-16,17,18,19-tetrahydro-rifamycin SV (mixture of epimers); the mass spectrum: m/z=952 (M+1)+ corresponds to the empirical formula $C_{54}H_{69}N_3O_{12}$.

EXAMPLE 4

A solution of 2 g of 3-[4-(4-biphenylylmethyl)-1-piperazinyl]-rifamycin SV in 100 ml of ethanol is hydrogenated in the presence of 0.2 g of platinum oxide for 4 hours at room temperature under normal pressure. The reaction mixture is worked up analogously to Example 1, yielding 3-[4-(4-biphenylyl-methyl)-1piperazinyl]-16,17,18,19,28,29-hexahydro-rifamycin SV (mixture of epimers); the mass spectrum (m/z=954 (M+1)+) thereof corresponds to the empirical formula $C_{54}H_{71}N_3O_{12}$.

EXAMPLE 5

3-[4-(4-biphenylyl-methyl)-1-piperazinyl]-16,17,18,19-tetrahydro-rifamycin SV is obtained analogously to Example 2 from 16,17,18,19-tetrahydrorifamycin S and 1-(4-biphenylyl-methyl)-piperazine.

EXAMPLE 6

Capsules, each containing 250 mg of 3-[4(4-biphenylyl-methyl)-1-piperazinyl]-rifamycin SV, can be prepared as follows:

| Composition (for 1000 capsules): | |
|---|---|
| 3-[4-(4-biphenylyl-methyl)-1-piperazinyl]-rifamycin SV | 250.0 g |
| corn starch | 50.0 g |
| polyvinylpyrrolidone | 15.0 g |
| magnesium stearate | 5.0 g |
| ethanol | q.s. |

The active ingredient and the corn starch are mixed and and the mixture is moistened with a solution of the polyvinylpyrrolidone in 50 g of ethanol. The moist mass is pressed through a sieve of mesh width 3 mm and dried at 45°. The dry granulate is sieved through a sieve of mesh width 1 mm and mixed with 5 g of magnesium stearate. The mixture is introduced into size 0 dry-fill capsules in portions of 0.320 g.

What is claimed is:

1. Rifamycin derivative of the formula

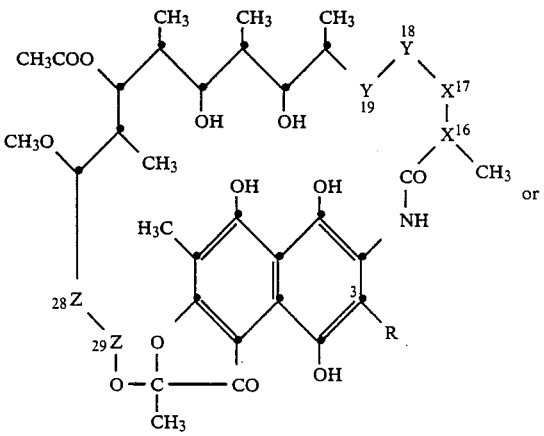

(IA)

-continued

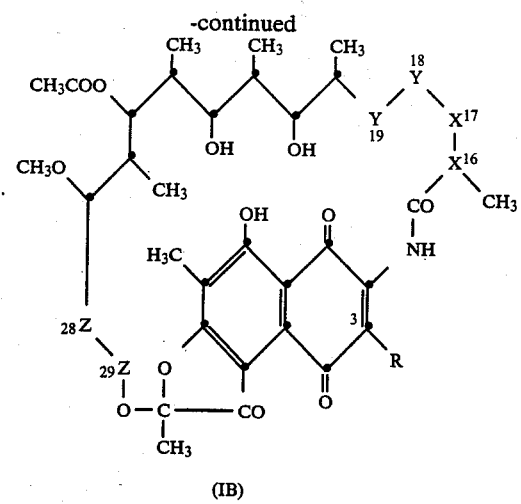

(IB)

wherein R is a radical of the formula

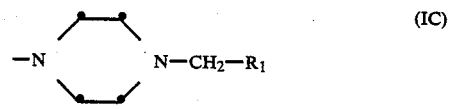

(IC)

in which $R_1$ is an unsubstituted or is substituted biphenylyl radical, or is substituted by lower alkyl, lower alkoxy, or by halogen and wherein X—X, Y—Y and Z—Z are each vinylene of the formula CH=CH, or wherein X—X and Y—Y are each ethylene of the formula $CH_2$—$CH_2$ and Z—Z is ethylene or vinylene, and a salt of such compounds.

2. A compound according to claim 1, wherein $R_1$ is a 2-or 4-biphenylyl radical which is unsubstituted or is substituted by lower alkyl having up to and including 4 carbon atoms, lower alkoxy having up to and including 4 carbon atoms, or by halogen, especially by methyl, methoxy, fluorine or chlorine, or a salt thereof.

3. A compound according to claim 1, wherein $R_1$ is unsubstituted 4-biphenylyl, or a salt thereof.

4. A compound of formula IA according to claim 1 or a salt thereof.

5. A compound according to claim 1, wherein X—X, Y—Y and Z—Z are each vinylene, or a pharmaceutically acceptable salt thereof.

6. A compound according to claim 1, wherein X—X and Y—Y are each ethylene and Z-Z is vinylene, or a pharmaceutically acceptable salt thereof.

7. A compound according to claim 1, wherein X—X, Y—Y and Z—Z are each ethylene, or a pharmaceutically acceptable salt thereof.

8. 3-[4-(4-Biphenylyl-methyl)-1-piperazinyl]-rifamycin SV or a pharmaceutically acceptable salt thereof according to claim 1.

9. 3-[4-(4-Biphenylyl-methyl)-1-piperazinyl]-16,17,18,-19-tetrahydro-rifamycin SV or a pharmaceutically acceptable salt thereof according to claim 1.

10. 3-[4-(4-Biphenylyl-methyl)-1-piperazinyl]-16,17,18,-19,28,29-hexahydro-rifamycin SV or a pharmaceutically acceptable salt thereof according to claim 1.

11. A pharmaceutical composition containing as active ingredient a pharmaceutically effective amount of a compound defined in claim 1 or a pharmaceutically acceptable salt thereof together with a pharmaceutically acceptable carrier.

12. A therapeutic method for the treatment of bacterial disease or viral diseases caused by type C retroviruses which comprises administering to a warm-blooded animal, included humans, an effective dose of a compound defined in claim 1 or a pharmaceutically acceptable salt thereof.

* * * * *